United States Patent
Lee et al.

(10) Patent No.: US 10,439,142 B2
(45) Date of Patent: Oct. 8, 2019

(54) ORGANIC SOLAR CELL AND MANUFACTURING METHOD THEREFOR

(71) Applicant: LG CHEM, LTD., Seoul (KR)

(72) Inventors: Hangken Lee, Daejeon (KR); Jiyoung Lee, Daejeon (KR); Jaechol Lee, Daejeon (KR); Songrim Jang, Daejeon (KR); Doowhan Choi, Daejeon (KR); Jiwon Bang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 308 days.

(21) Appl. No.: 15/303,712

(22) PCT Filed: Apr. 30, 2015

(86) PCT No.: PCT/KR2015/004404
§ 371 (c)(1),
(2) Date: Oct. 12, 2016

(87) PCT Pub. No.: WO2015/167284
PCT Pub. Date: Nov. 5, 2015

(65) Prior Publication Data
US 2017/0040543 A1    Feb. 9, 2017

(30) Foreign Application Priority Data
Apr. 30, 2014    (KR) .................. 10-2014-0052648

(51) Int. Cl.
*H01L 51/00*    (2006.01)
*C09K 11/06*    (2006.01)
(Continued)

(52) U.S. Cl.
CPC ........ *H01L 51/0047* (2013.01); *C07D 323/00* (2013.01); *C09K 11/06* (2013.01);
(Continued)

(58) Field of Classification Search
CPC .......... H01L 51/42–448; H01L 51/0046–0047
See application file for complete search history.

(56) References Cited

U.S. PATENT DOCUMENTS 8,969,718 B2    3/2015   Iwanaga et al.
9,711,729 B2 *  7/2017   Bae .................... H01L 51/0047
(Continued)

FOREIGN PATENT DOCUMENTS

CN    104779351    8/2017
EP    2975663      1/2016
(Continued)

OTHER PUBLICATIONS

Liao, et al. "Multiple functionalities of polyfluorene grafted with metal ion-intercalated crown ether as an electron transport layer for bulk-heterojunction polymer solar cells" Journal of the American Chemical Society 134.35 (2012). Plus supplementary Information.*
(Continued)

*Primary Examiner* — Angelo Trivisonno
*Assistant Examiner* — William E McClain
(74) *Attorney, Agent, or Firm* — Myers Bigel, P.A.

(57) ABSTRACT

The present specification relates to an organic solar cell and a method for manufacturing the same.

18 Claims, 2 Drawing Sheets

(51) Int. Cl.
    H01L 51/42    (2006.01)
    C07D 323/00   (2006.01)
(52) U.S. Cl.
    CPC ...... *H01L 51/0036* (2013.01); *H01L 51/0037* (2013.01); *H01L 51/42* (2013.01); *H01L 51/4246* (2013.01); *H01L 51/4253* (2013.01)

(56) References Cited

U.S. PATENT DOCUMENTS

| | | | |
|---|---|---|---|
| 2012/0004476 A1 | 1/2012 | Yoon et al. | |
| 2012/0204958 A1 | 8/2012 | Lin et al. | |
| 2013/0074920 A1 | 3/2013 | Echegoyen et al. | |
| 2013/0140527 A1* | 6/2013 | Chen | H01L 51/0035 257/40 |
| 2013/0327376 A1 | 12/2013 | Bulliard et al. | |
| 2015/0107674 A1 | 4/2015 | Lee et al. | |
| 2016/0087213 A1* | 3/2016 | Bae | H01L 51/0047 257/40 |

FOREIGN PATENT DOCUMENTS

| | | |
|---|---|---|
| JP | 2012162506 A | 8/2012 |
| JP | 2012169618 A | 9/2012 |
| JP | 2012230992 A | 11/2012 |
| JP | 2013157635 A | 8/2013 |
| JP | 2013203881 A | 10/2013 |
| KR | 101059783 B1 | 8/2011 |
| KR | 1020120003672 A | 1/2012 |
| KR | 1020130133571 A | 12/2013 |
| KR | 1020130137889 A | 12/2013 |

OTHER PUBLICATIONS

Cheng, et al. "Combination of indene-C60 bis-adduct and cross-linked fullerene interlayer leading to highly efficient inverted polymer solar cells." Journal of the American Chemical Society 132.49 (2010): 17381-17383.*

Lai, Yu-Ying, Yen-Ju Cheng, and Chain-Shu Hsu. "Applications of functional fullerene materials in polymer solar cells." Energy & Environmental Science 7.6 (2014): 1866-1883.*

Zhang, et al. "Poly (ethylene glycol) modified [60] fullerene as electron buffer layer for high-performance polymer solar cells." Applied Phy.*

Meijer, et al. "Metal-chelating capacities attached to fullerenes." Coordination chemistry reviews 230.1-2 (2002): 141-163.*

Tzirakis, et al. "Photochemical addition of ethers to C60: Synthesis of the simplest [60] fullerene/crown ether conjugates." Angewandte Chemie International Edition 49.34 (2010): 5891-5893. (Year: 2010).*

Lu et al. "Co-Catalyzed Radical Cycloaddition of [60]Fullerene with Active Dibromides: Selective Synthesis of Carbocycle-Fused Fullerene Monoadducts" Organic Letters 15(15):4030-4033 (2013).

Tzeli et al. "A Theoretical Study of Complexes of Crown Ethers with Substituted Ammonium Cations" Progress in Theoretical Chemistry and Physics 22:599-610 (2012).

Tzirakis et al. "Photochemical Addition of Ethers to C60:Synthesis of the Simplest [60]Fullerene/Crown Ether Conjugates" Angewandte Chemie International Edition 49(34):5891-5893 (2010).

European Search Report corresponding to European Patent Application No. 15/785539.6, dated Nov. 15, 2017, 9 pages.

Jae Woong Jung et al: "Enhanced Performance and Air Stability of Polymer Solar Cells by Formation of a Self-Assembled Buffer Layer from Fullerene-End-Capped Poly(ethylene glycol)", Advanced Materials, vol. 23, No. 15, Mar. 1, 2011, pp. 1782-1787.

Qidong Tai et al: "Enhanced photovoltaic performance of polymer solar cells by adding fullerene end-capped polyethylene glycol", Journal of Materials Chemistry, vol. 21, No. 19, Apr. 4, 2011, p. 6848

Sih-Hao Liao et al: "Multiple Functionalities of Polyfluorene Grafted with Metal Ion-Intercalated Crown Ether as an Electron Transport Layer for Bulk-Heterojunction Polymer Solar Cells: Optical Interference, Hole Blocking, Interfacial Dipole, and Electron Conduction"; Journal of the American Chemical Society, vol. 134, No. 35, Aug. 17, 2012, pp. 14271-14274.

Xiaodong Liu et al: "Crown-ether functionalizeci fullerene as a solution-processable cathode buffer layer for high performance perovskite and polymer solar cells", Journal of Materials Chemistry A: Materials for Energy and Sustainability, vol. 3, No. 17, Mar. 16, 2015, pp. 9278-9284.

C. W. Tang, "Two-layer organic photovoltaic cell", Appl. Phys. Lett., 48, 183. (1996)).

G. Yu, et al., "Efficiencies via Network of Internal Donor-Acceptor Heterojunctions", Science, 270, 1789. (1995)).

Francis D'Souza, et al., "Supramolecular Carbon Nanotube-Fullerene Donor-Acceptor Hybrids for Photoinduced Electron Transfer" J.Am.Chem.Soc. 2007, 129, 15865-15871.

* cited by examiner

[Figure 1]
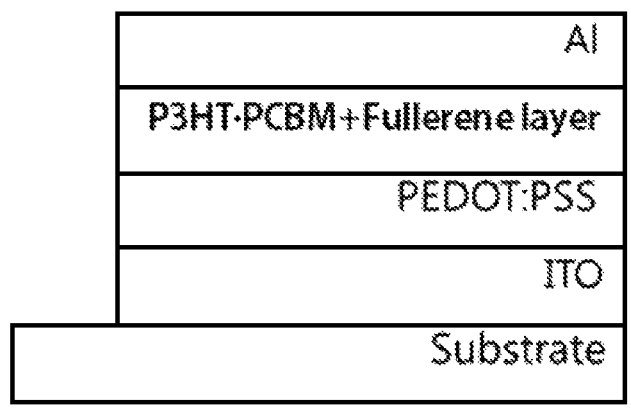
[Figure 2]
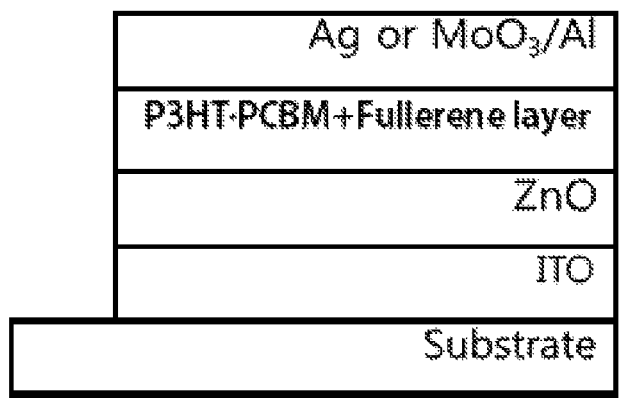

[Figure 3]
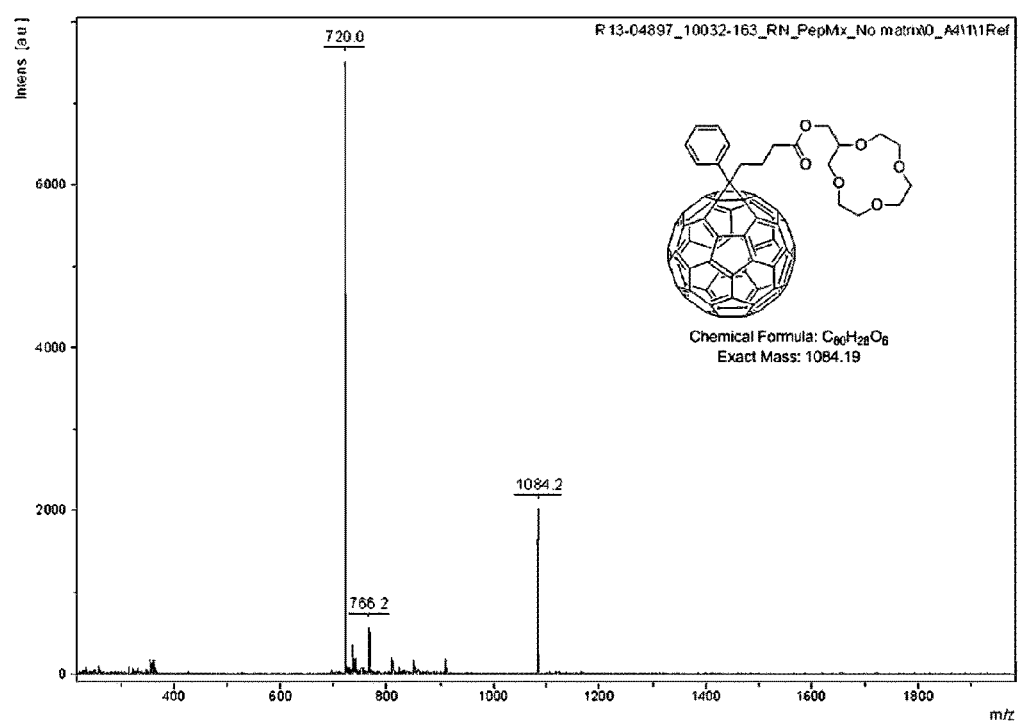

ORGANIC SOLAR CELL AND MANUFACTURING METHOD THEREFOR

This application is a National Stage Application of International Application No. PCT/KR2015/004404, filed Apr. 30, 2015, and claims the benefit of Korean Patent Application No. 10-2014-0052648, filed Apr. 30, 2014, the contents of which are incorporated herein by reference in their entirety for all purposes as if fully set forth below.

TECHNICAL FIELD

This specification claims priority to and the benefit of Korean Patent Application No. 10-2014-0052648 filed in the Korean Intellectual Property Office on Apr. 30, 2014, the entire contents of which are incorporated herein by reference.

The present specification relates to an organic solar cell and a method for manufacturing the same.

BACKGROUND ART

According to an energy review material by a US National Laboratory NREL, the energy sources, which are currently mainly used, are petroleum, coal, and gas. These energy sources amount to 80% of the total energy source which is used. However, the current depletion state of petroleum and coal energy is gradually becoming a big problem, and an increase in emission of carbon dioxide and other greenhouse gases into the air is generating increasingly severe problems. In contrast, the use of renewable energy which is non-polluting green energy is yet about 2% of the total energy source. Thus, worries about solving the problems of the energy source more and more have become a motivation for promoting studies for developing new renewable energy. Among the new renewable energy sources such as wind, water, and the sun, solar energy is drawing the most attention. Solar cells using solar energy produce less pollution, are limitless in terms of resources, have a semi-permanent lifetime, and thus are expected as an energy source capable of solving the future energy problems.

A solar cell is a device which may directly convert solar energy into electric energy by applying a photovoltaic effect. The solar cell may be divided into an inorganic solar cell and an organic solar cell, depending on the materials constituting a thin film. Typical solar cells are made through a p-n junction by doping crystalline silicon (Si), which is an inorganic semiconductor. Electrons and holes generated by absorbing light diffuse to p-n junction points and move to an electrode while being accelerated by the electric field. The power conversion efficiency in this process is defined as the ratio of electric power given to an external circuit and solar power entering the solar cell, and the efficiency have reached approximately 24% when measured under a currently standardized virtual solar irradiation condition. However, since inorganic solar cells in the related art already have shown the limitation in economic feasibility and material demands and supplies, an organic solar cell, which is easily processed and inexpensive and has various functionalities, has come into the spotlight as a long-term alternative energy source.

For the early organic solar cell, the group of Professor Heeger at UCSB of USA initiatively led the development of technology. The organic solar cell has an advantage in that monomolecular organic materials or polymer materials used easily and quickly enable an inexpensive and large area process.

However, according to the studies, which have been conducted until now, the organic solar cell has a disadvantage in that the energy conversion efficiency is low. Therefore, in order to secure the competitiveness with other solar cells at this point, it can be said that an improvement in efficiency is very important.

DETAILED DESCRIPTION OF THE INVENTION

Technical Problem

An object of the present specification is to provide an organic solar cell and a method for manufacturing the same.

Technical Solution

The present specification provides a solar cell including:
a first electrode;
a second electrode provided to face the first electrode;
a photoactive layer provided between the first electrode and the second electrode; and
a layer including a fullerene derivative provided to be in contact with the photoactive layer,
in which the fullerene derivative has a crown-type substituent.

Further, the present specification provides a method for manufacturing the above-described organic solar cell, the method including: preparing a substrate;
forming a first electrode on the substrate;
forming an organic material layer having two or more layers, which includes a photoactive layer and a layer including a fullerene derivative having a crown-type substituent, on the first electrode; and
forming a second electrode on the organic material layer.

Advantageous Effects

In the case of including a layer including the fullerene derivative according to the present specification, the light absorbance is increased, the recombination of charges is suppressed, and transport characteristics of current are improved. Accordingly, an organic solar cell according to an exemplary embodiment of the present specification may implement an increase in short-circuit current density (Jsc) and an increase in efficiency.

Further, the fullerene derivative is provided to be in contact with a photoactive layer, and thus may lower the charge transfer barrier between the photoactive layer and a charge transport layer and may improve the contact. In this case, the fill factor (FF) may be improved to implement a high efficiency.

A layer including the fullerene derivative according to an exemplary embodiment of the present specification may include an ionic group. In this case, light absorption may be increased via redistribution of incident light, and the barrier of charges may be adjusted due to an increase in interfacial dipole. In addition, it is possible to expect an organic solar cell with high efficiency due to an increase in conductivity.

The organic solar cell according to an exemplary embodiment of the present specification may provide a uniform buffer layer while maintaining a thin thickness by a method for simultaneously manufacturing a photoactive layer and a layer including a fullerene derivative. Further, due to a simple manufacturing process, it is possible to reduce production costs and/or increase the efficiency of the process.

The organic solar cell according to an exemplary embodiment of the present specification may have a wound structure, and when the structure is in a cylindrical form, the organic solar cell may efficiently absorb light in various directions to increase the efficiency.

BRIEF DESCRIPTION OF DRAWINGS

FIGS. 1 and 2 illustrate an organic solar cell according to an exemplary embodiment.

FIG. 3 is a view illustrating the MS spectrum of a fullerene derivative of Chemical Formula 2-2-1.

BEST MODE

Hereinafter, the present specification will be described in more detail.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

An exemplary embodiment of the present specification provides an organic solar cell comprising: a first electrode; a second electrode provided to face the first electrode; a photoactive layer provided between the first electrode and the second electrode; and a layer including a fullerene derivative provided to be in contact with the photoactive layer, in which the fullerene derivative has a crown-type substituent.

In an exemplary embodiment of the present specification, the layer including the fullerene derivative includes a self-phase separation unit. The self-phase separation unit includes a hydrophobic or hydrophilic substituent.

In the present specification, the self-phase separation unit is a crown-type substituent.

In an exemplary embodiment of the present specification, the photoactive layer includes a photoactive layer material including one or two more materials selected from the group consisting of electron acceptor materials and electron donor materials, and the layer including the fullerene derivative is formed by the phase separation of the photoactive layer material and a material for the layer including a fullerene derivative.

In an exemplary embodiment of the present specification, at the boundary of the two layers formed by the phase separation, the materials for the two layers may be partially mixed with each other. This case allows a change in energy level to be generated in a cascade mode. Accordingly, this case may be advantageous in transporting charges and collecting charges. Furthermore, since a material for a layer including a fullerene derivative is present on the surface of the photoactive layer due to the phase separation, a change in surface energy may occur due to the vacuum level shift.

In an exemplary embodiment of the present specification, the content of the fullerene derivative having the crown-type substituent at the interface of the photoactive layer and the layer including the fullerene derivative, which are formed by the phase separation is 1 wt % to 15 wt %, and preferably 3 wt % to 7 wt %, based on the total content of the photoactive layer material.

In an exemplary embodiment of the present specification, when the content of the fullerene derivative having the crown-type substituent at the interface of the photoactive layer and the layer including the fullerene derivative, which are formed by the phase separation, is 15 wt % or more, there is an effect in that the thickness of the phase-separated layer becomes larger than the optical thickness or the aggregation phenomenon in the photoactive layer occurs, and thus charges may be trapped, or when the content is 1 wt % or less, it is difficult to form a single layer due to the phase separation, but there is a weak effect of an increase in transporting charges caused by doping.

The "phase separation" in the present specification means that two or more materials are separated from each other without a separate process by different affinities in a uniform mixed state to form a layer phase.

Specifically, a material including the fullerene derivative may be separated by increasing the amount of the hydrophilic crown-type substituent to enhance the hydrophilicity, and may be separated by introducing hydrophobic substituent into the fullerene derivative to enhance the hydrophobicity.

In an exemplary embodiment of the present specification, the photoactive layer and the layer including the fullerene derivative are provided to be in contact with each other. To be provided to be in contact with each are not limited to a physical bond or a chemical bond.

In an exemplary embodiment of the present specification, the photoactive layer and the layer including the fullerene derivative are simultaneously formed to be in contact with each other by using the self-phase separation of the photoactive layer and the layer including the fullerene derivative.

In an exemplary embodiment of the present specification, the layer including the fullerene derivative is provided on one surface of the photoactive layer which is close to a first electrode. In another exemplary embodiment, the layer including the fullerene derivative is provided on one surface of the photoactive layer which is close to a second electrode.

The layer including the fullerene derivative may also be applied to a normal structure, and may also be applied to an inverted structure.

In an exemplary embodiment of the present specification, the layer including the fullerene derivative serves as a buffer layer. The layer including the fullerene derivative may serve to facilitate the movement of electrons between the photoactive layer and the charge transport layer. Further, the layer including the fullerene derivative may serve to facilitate the movement of charges between the charge transport layer and the first electrode or the second electrode.

In an exemplary embodiment of the present specification, the layer including the fullerene derivative and formed by the phase separation has a thickness of 1 nm to 30 nm. The thickness is preferably 3 nm to 10 nm. The thickness within the range may be helpful in the formation of the morphology of the photoactive layer to increase the mobility of charges and enhance the open-circuit voltage and the ability to collect charges due to the formation of dipoles at the interface, thereby increasing the density of current. Further, the fill factor may be enhanced by preventing the recombination of charges.

When the layer including the fullerene derivative has a thickness of more than 30 nm, there occurs a problem in that the density of current is decreased due to a decrease in mobility of charges, and the fill factor deteriorates due to an increase in recombination of charges.

In an exemplary embodiment of the present specification, the layer including the fullerene derivative includes one or two or more fullerene derivatives selected from the group consisting of fullerene derivatives represented by the following Chemical Formula 1 to 3.

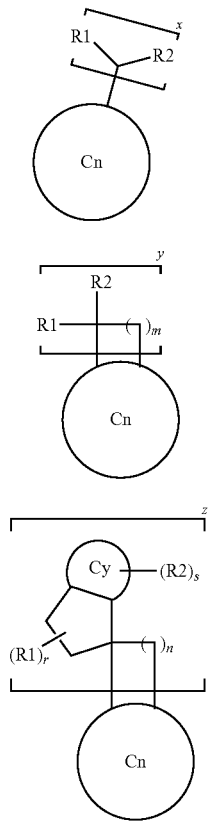

[Chemical Formula 1]

[Chemical Formula 2]

[Chemical Formula 3]

In Chemical Formula 1 to 3,

Cn is a $C_{60}$ to C120 fullerene, m and n are each an integer of 0 to 3, x, y, and z are each an integer of 1 to 10, at least one of R1 and R2 is -(L)a-(Y), a is an integer of 0 to 4, when a is 2 or more, two or more L's are the same as or different from each other, L is a substituted or unsubstituted divalent ester group; a substituted or unsubstituted divalent thioester group; a substituted or unsubstituted divalent thionoester group; a divalent ketone group; a divalent thione group; a divalent carbonyl group; a substituted or unsubstituted alkylene group; a substituted or unsubstituted alkenylene group; a substituted or unsubstituted arylene group; or a substituted or unsubstituted divalent hetero-cyclic group, Y is a crown-type substituent, Cy is a substituted or unsubstituted monocyclic or polycyclic aromatic hydrocarbon ring; or a substituted or unsubstituted monocyclic or polycyclic hetero ring, the other R's in R1 and R2 are the same as or different from each other, and each independently hydrogen; a halogen group; a carboxylic acid group; a nitro group; a nitrile group; an imide group; an amide group; an imine group; thioimide; an anhydride group; a hydroxy group; a substituted or unsubstituted ester group; a substituted or unsubstituted thioester group; a substituted or unsubstituted thionoester group; a substituted or unsubstituted carbonyl group; a substituted or unsubstituted thione group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted hetero-cyclic group, and R1 and R2 in Chemical Formula 3 may combine with each other to form a monocyclic or polycyclic ring, r is an integer of 0 to 2, s is an integer of 0 to 30, when r and s are each 2 or more, the structures in the parenthesis are the same as or different from each other, and Chemical Formula 1 to 3 may be additionally unsubstituted or substituted with a substituent selected from the group consisting of hydrogen; a halogen group; a carboxylic acid group; a nitro group; a nitrile group; an imide group; an amide group; an imine group; thioimide; an anhydride group; a hydroxy group; a substituted or unsubstituted ester group; a substituted or unsubstituted thioester group; a substituted or unsubstituted thionoester group; a substituted or unsubstituted carbonyl group; a substituted or unsubstituted thione group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; and a substituted or unsubstituted hetero-cyclic group.

In an exemplary embodiment of the present specification, the number of carbon atoms of the crown-type substituent is 8 to 40.

In an exemplary embodiment of the present specification, Y is represented by the following structure.

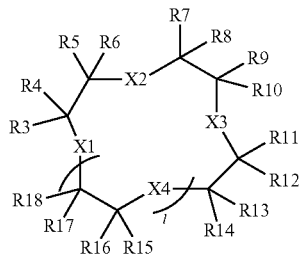

In the structure, l is a repeating number of a structure in the parenthesis and is an integer of 1 to 3, and when l is 2 or more, two or more structures in the parenthesis are the same as or different from each other, X1 to X4 are the same as or different from each other, and each independently O, S, or NR, R and R3 to R18 are the same as or different from each other, and each independently hydrogen; a halogen group; a carboxylic acid group; a nitro group; a nitrile group; an imide group; an amide group; an imine group; thioimide; an anhydride group; a hydroxy group; a substituted or unsubstituted ester group; a substituted or unsubstituted thioester group; a substituted or unsubstituted thionoester group; a substituted or unsubstituted carbonyl group; a substituted or unsubstituted thione group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted hetero-cyclic group, or adjacent groups combine with each other to form a substituted or unsubstituted hydrocarbon ring; or a substituted or unsubstituted hetero ring, and one of R3 to R18 combines with the fullerene derivative through -(L)a-.

In an exemplary embodiment of the present specification, L is a substituted or unsubstituted divalent ester group; a substituted or unsubstituted alkylene group; or a substituted or unsubstituted arylene group.

In another exemplary embodiment, a is an integer of 2 or more, and the two or more L's are the same as or different from each other, and each independently include a divalent ester group; and a substituted or unsubstituted alkylene group.

In still another exemplary embodiment, -(L)a- is

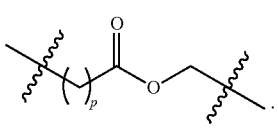

p is an integer of 0 to 30.

In yet another exemplary embodiment, p is 3.

In an exemplary embodiment of the present specification, a is an integer of 2 or more, and the two or more L's are the same as or different from each other, and each independently include a divalent ester group; and a substituted or unsubstituted arylene group.

In another exemplary embodiment, -(L)a- is

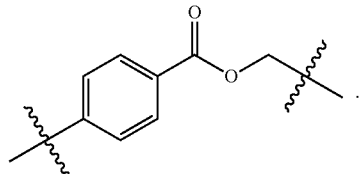 [SMILES: *COC(=O)c1ccc(*)cc1]

In an exemplary embodiment of the present specification, the rest other than -(L)a-(Y) in R1 and R2 is hydrogen; or a substituted or unsubstituted ester group.

In one exemplary embodiment, the rest other than -(L)a-(Y) in R1 and R2 is hydrogen.

In another exemplary embodiment, the rest other than -(L)a-(Y) in R1 and R2 is a substituted or unsubstituted ester group.

In one exemplary embodiment, the rest other than -(L)a-(Y) in R1 and R2 is an ester group which is substituted with an alkyl group.

In another exemplary embodiment, the rest other than -(L)a-(Y) in R1 and R2 is an ester group which is substituted with a methyl group.

In still another exemplary embodiment, the rest other than -(L)a-(Y) in R1 and R2 is a substituted or unsubstituted aryl group.

In yet another embodiment, the rest other than -(L)a-(Y) in R1 and R2 is a phenyl group.

In an exemplary embodiment of the present specification, X1 is O.

In another exemplary embodiment, X2 is O.

In an exemplary embodiment of the present specification, X3 is O.

In another exemplary embodiment, X4 is O.

In an exemplary embodiment of the present specification, at least one of X1 to X4 is O.

In an exemplary embodiment of the present specification, Cy of Chemical Formula 3 is a substituted or unsubstituted benzene; a substituted or unsubstituted naphthalene; or a substituted or unsubstituted hetero ring.

In an exemplary embodiment of the present specification, Cy of Chemical Formula 3 includes a substituted or unsubstituted benzene, a substituted or unsubstituted naphthalene, or at least one of O, S, and N, and is a substituted or unsubstituted hetero ring.

In an exemplary embodiment of the present specification, Cy of Chemical Formula 3 is benzene; naphthalene; or a hetero ring.

In an exemplary embodiment of the present specification, Cy of Chemical Formula 3 is benzene, naphthalene, or a hetero ring including at least one of O, S, and N.

In an exemplary embodiment of the present specification, Chemical Formula 3 may be represented by the following Chemical Formula 3a.

[Chemical Formula 3a]

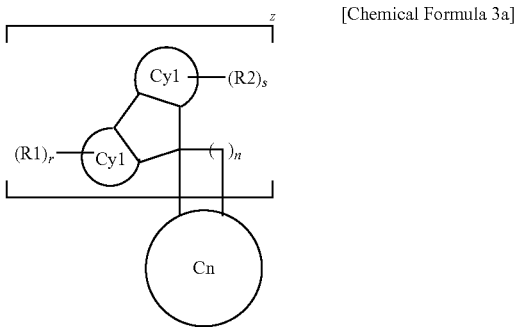

In Chemical Formula 3a, Cy1 and Cy2 are the same as or different from each other, and each a substituted or unsubstituted monocyclic or polycyclic aromatic hydrocarbon ring; or a substituted or unsubstituted monocyclic or polycyclic hetero ring, and the definitions of R1, R2, n, z, Cn, r, and s are the same as those described in Chemical Formula 3.

In an exemplary embodiment of the present specification, Chemical Formula 3 may be represented by the following Chemical Formula 3b.

[Chemical Formula 3b]

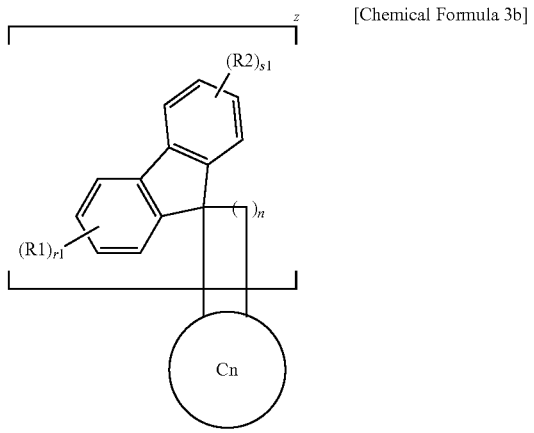

In Chemical Formula 3b, the definitions of R1, R2, n, z, and Cn are the same as those described in Chemical Formula 3, and r1 and r2 are an integer of 0 to 4, and when r1 and r2 are each 2 or more, the structures in the parenthesis are the same as or different from each other.

In an exemplary embodiment of the present specification, in Chemical Formula 3, Cy includes at least one of O, S, and N, and is a substituted or unsubstituted monocyclic or polycyclic hetero ring.

In an exemplary embodiment of the present specification, in Chemical Formula 3, Cy includes at least one of O, S, and N, and is a substituted or unsubstituted monocyclic hetero ring.

In an exemplary embodiment of the present specification, in Chemical Formula 3, Cy is a substituted or unsubstituted thiophene, a substituted or unsubstituted furan, a substituted or unsubstituted pyrrole, or a substituted or unsubstituted imidazole.

In an exemplary embodiment of the present specification, in Chemical Formula 3, Cy is thiophene, furan, pyrrole, or imidazole.

In an exemplary embodiment of the present specification, in Chemical Formula 3a, at least one of Cy1 and Cy2 includes at least one of O, S, and N and is a substituted or unsubstituted monocyclic or polycyclic hetero ring, and the other is a substituted or unsubstituted monocyclic or polycyclic aromatic hydrocarbon ring or a substituted or unsubstituted monocyclic or polycyclic hetero ring.

In an exemplary embodiment of the present specification, in Chemical Formula 3a, at least one of Cy1 and Cy2 includes at least one of O, S, and N and is a substituted or unsubstituted monocyclic or polycyclic hetero ring, and the other is a substituted or unsubstituted benzene.

In an exemplary embodiment of the present specification, in Chemical Formula 3a, at least one of Cy1 and Cy2 includes at least one of O, S, and N and is a substituted or unsubstituted monocyclic hetero ring, and the other is a substituted or unsubstituted benzene.

In an exemplary embodiment of the present specification, in Chemical Formula 3, at least one of Cy1 and Cy2 is a substituted or unsubstituted thiophene, a substituted or unsubstituted furan, a substituted or unsubstituted pyrrole, or a substituted or unsubstituted imidazole, and the other is a substituted or unsubstituted benzene.

In an exemplary embodiment of the present specification, in Chemical Formula 3a, at least one of Cy1 and Cy2 is thiophene, furan, pyrrole or imidazole, and the other is benzene.

In an exemplary embodiment of the present specification, the fullerene derivatives represented by Chemical Formula 1 to 3 are represented by the following Chemical Formula 1-1, Chemical Formula 2-1, Chemical Formula 2-2, and Chemical Formula 3-1.

[Chemical Formula 1-1]

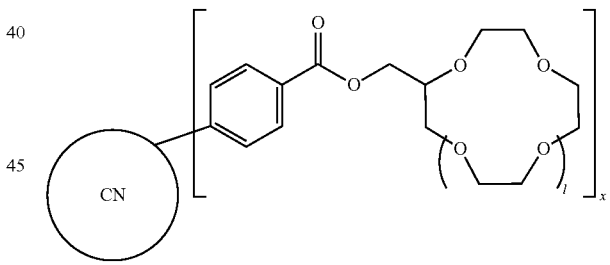

[Chemical Formula 2-1]

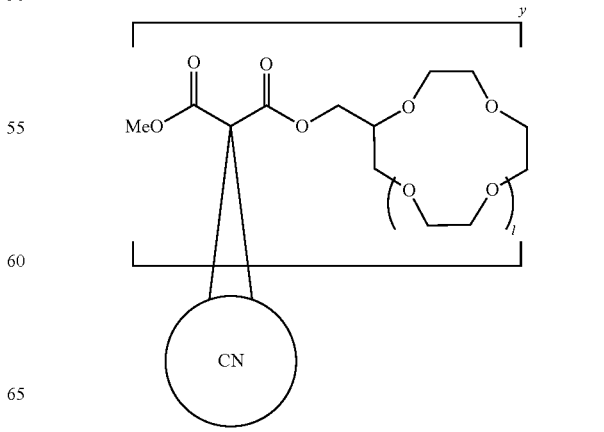

[Chemical Formula 2-2]

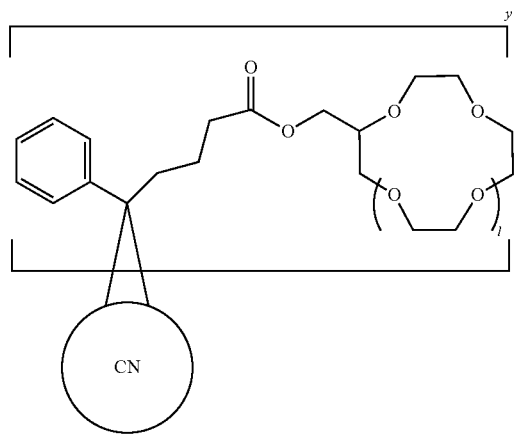

[Formula 2-2-1]

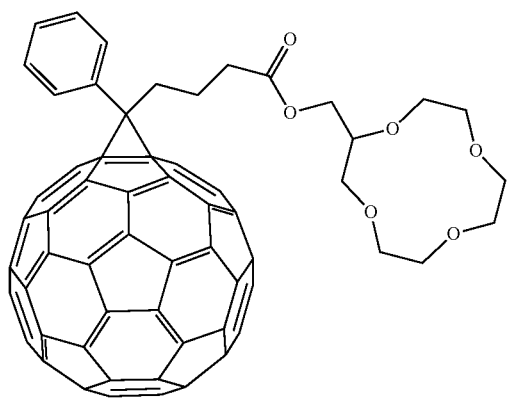

[Chemical Formula 3-1]

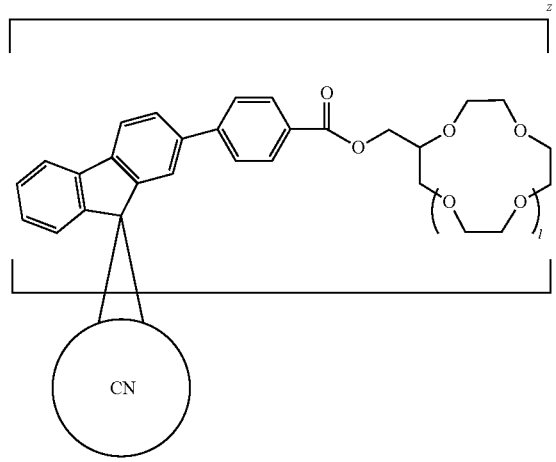

In Chemical Formula 1-1, 2-1, 2-2, and 3-1,

Cn, l, x, y, and z are the same as those described above.

In an exemplary embodiment of the present specification, Cn is a C60 fullerene derivative.

In another exemplary embodiment, l is 1.

In an exemplary embodiment of the present specification, in any one of Chemical Formula 1 and 1-1, x is 1 to 10, 1 to 7, 1 to 5, 1 to 3, or 1.

In an exemplary embodiment of the present specification, in any one of Chemical Formula 2, 2-1, and 2-2, y is 1 to 10, 1 to 7, 1 to 5, 1 to 3, or 1.

In an exemplary embodiment of the present specification, in any one of Chemical Formula 3 and 3-1, z is 1 to 10, 1 to 7, 1 to 5, 1 to 3, or 1.

In one exemplary embodiment, the fullerene derivative represented by Chemical Formula 2-2 may be represented by the following Chemical Formula 2-2-1.

An exemplary embodiment of the present specification further includes an ionic group provided at the center of the crown-type substituent. That is, an ionic group is provided in an empty space at the center of the crown-type substituent, and forms a chemical bond. In an exemplary embodiment of the present specification, two or more molecules in addition to only the single molecule of the crown-type substituent may form a 3-D structure to participate in the binding of ions.

However, the person skilled in the art may perform a heat treatment or UV treatment, if necessary, to crosslink fullerene derivatives having a plurality of crown-type substituents.

In one exemplary embodiment, the crown-type substituent including the ionic group may be represented as follows.

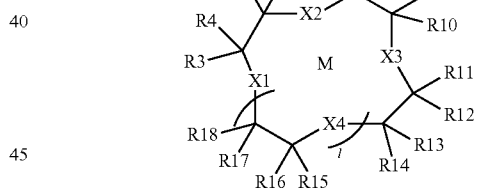

In the structure, R3 to R18, l, and X1 to X4 are the same as those described above, and M is an ionic group.

In an exemplary embodiment of the present specification, the number of ions of a metal to be inserted and the type of metal may be selected by adjusting the repeating number of l, that is, the size of the crown-type substituent.

In the case of including an ionic group as described above, light absorption may be increased via redistribution of incident light, and the barrier of charges may be adjusted due to an increase in interfacial dipole. In addition, it is possible to expect an organic solar cell with high efficiency due to an increase in conductivity.

In the present specification, the ionic group may be a positive ionic group or a negative ionic group.

In an exemplary embodiment of the present specification, the ionic group may include one molecule, and also includes the case where two or more molecules form a 3-D structure and are bonded to each other.

In an exemplary embodiment of the present specification, the ionic group is a positive ion of a metal selected from the group consisting of titanium (Ti), zirconium (Zr), strontium (Sr), zinc (Zn), indium (In), lanthanum (La), vanadium (V), molybdenum (Mo), tungsten (W), tin (Sn), niobium (Nb), magnesium (Mg), calcium (Ca), barium (Ba), aluminum (Al), yttrium (Y), scandium (Sc), samarium (Sm), gallium (Ga), potassium (K), cobalt (Co), copper (Cu), silver (Ag), sodium (Na), and lead (Pb); an ammonium ion selected from the group consisting of $NH_4^+$ and $CH_3NH_3^+$; or a negative ion selected from the group consisting of $N_3^-$, $CH_3CO_2^-$, $CN^-$, $Br^-$, $Cl^-$, $I^-$, $F^-$, $SCN^-$, $ClO_4^-$, $NO_3^-$, $CO_3^{2-}$, $SO_4^{2-}$, $PO_4^{3-}$, $H_2PO_4^{2-}$, $PdCl_6^{2-}$, $Na^-$, $Cs^-$, citric acid ion (citrate$^{3-}$), $SiF_5^-$, $SiF_6^{2-}$, $GeF_6^{2-}$, and $BF_4^-$.

Examples of the substituents will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

The term "substituted or unsubstituted" as used herein means being unsubstituted or substituted with one or more substituents selected from the group consisting of deuterium; a halogen group; an alkyl group; an alkenyl group; an alkoxy group; an ester group; a carbonyl group; a carboxyl group; a hydroxy group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a nitrile group; a nitro group; a hydroxy group; and a hetero-cyclic group, or being unsubstituted or substituted with the substituent to which two or more substituents are linked among the exemplified substituents. For example, "the substituent to which two or more substituents are linked" may be a biphenyl group. That is, the biphenyl group may also be an aryl group, and may be interpreted as a substituent to which two phenyl groups are linked.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the halogen group may be fluorine, chlorine, bromine, or iodine.

In the present specification, the number of carbon atoms of an imide group is not particularly limited, but is preferably 1 to 25. Specifically, the imide group may be a compound having the following structures, but is not limited thereto.

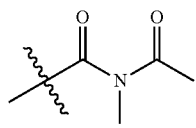

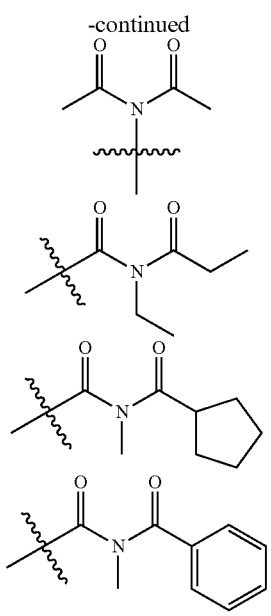

In the present specification, a thioimide group is a group in which C=O of the imide group is substituted with C=S.

In the present specification, an anhydride group is a group in which the N atom of the imide group is substituted with O.

In the present specification, for an amide group, one or two nitrogen atoms of the amide group may be substituted with hydrogen, a straight-chained, branched, or cyclic alkyl group having 1 to 25 carbon atoms, or an aryl group having 6 to 25 carbon atoms. Specifically, the amide group may be a compound having the following structural formula, but is not limited thereto.

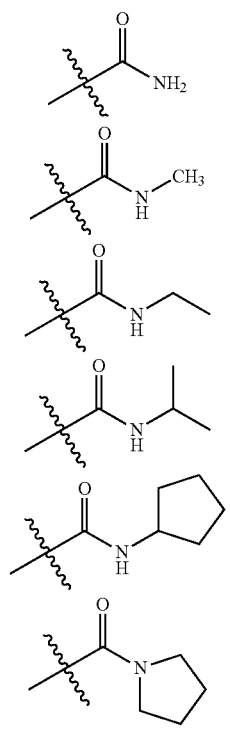

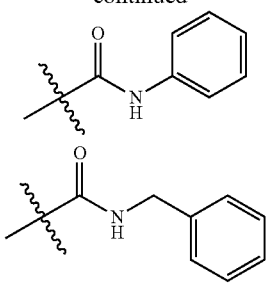

In the present specification, the amide group also includes a cyclic group such as lactam.

In the present specification, the general formula of an ester group may be represented by

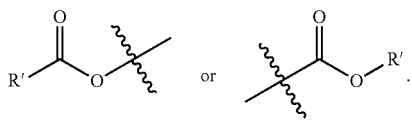

R' is hydrogen; an alkoxy group having 1 to 60 carbon atoms; a substituted or unsubstituted alkyl group having 1 to 60 carbon atoms; a substituted or unsubstituted cycloalkyl group having 3 to 60 carbon atoms; a substituted or unsubstituted arylalkyl group having 7 to 50 carbon atoms; a heteroarylalkyl group having 2 to 60 carbon atoms; a substituted or unsubstituted ester group having 1 to 40 carbon atoms; a substituted or unsubstituted carbonyl group having 1 to 40 carbon atoms; a substituted or unsubstituted aryl group having 6 to 60 carbon atoms; or a substituted or unsubstituted hetero-cyclic group having 2 to 60 carbon atoms, which includes one or more of N, O and S atoms.

The ester group of the present specification also includes a cyclic group such as a lactone group.

In the present specification, a thioester group is a group in which C=O of the ester group is substituted with C=S.

In the present specification, a carbonyl group may be represented by

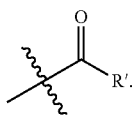

R' is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted hetero-cyclic group having 2 to 60 carbon atoms.

A thione group of the present specification is a group in which an O atom of the carbonyl group is substituted with an S atom.

In the present specification, an imine group may be represented by

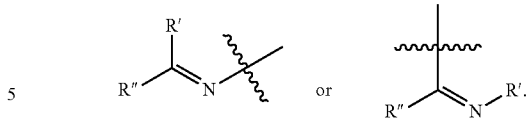

$R'$ and $R''$ are the same as or different from each other, and hydrogen; a substituted or unsubstituted straight-chained, branched, or cyclic alkyl group having 1 to 25 carbon atoms; or a substituted or unsubstituted aryl group having 6 to 25 carbon atoms.

In the present specification, the ether group may be represented by

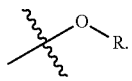

R is a substituted or unsubstituted straight-chained, branched, or cyclic alkyl group having 1 to 25 carbon atoms; or a substituted or unsubstituted aryl group having 6 to 25 carbon atoms. Specifically, Z1 to Z3 are the same as or different from each other, and a substituted or unsubstituted straight-chained, branched, or cyclic alkyl group having 6 to 25 carbon atoms; or a substituted or unsubstituted aryl group having 6 to 25 carbon atoms.

In the present specification,

means a moiety linked to another substituent.

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methyl-hexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the number of carbon atoms of the arylalkyl group is not particularly limited in, but in an exemplary embodiment of the present specification, the number of carbon atoms of the arylalkyl group is 7 to 50. Specifically, the number of carbon atoms of the aryl moiety is 6 to 49, and the number of carbon atoms of the alkyl moiety is 1 to 44. Specific examples thereof include a benzyl group, a p-methylbenzyl group, an m-methylbenzyl group, a p-ethylbenzyl group, an m-ethylbenzyl group, a 3,5-dimethylbenzyl group, an α-methylbenzyl group, an α,α-dimethylbenzyl group, an α,α-methylphenylbenzyl group, a 1-naphthylbenzyl group, a 2-naphthylbenzyl group, a p-fluorobenzyl group, a 3,5-difluorobenzyl group, an α,α-ditrifluoromethylbenzyl group, a p-methoxybenzyl group, an m-methoxybenzyl group, an α-phenoxybenzyl group, an α-benzyloxybenzyl group, a naphthylmethyl group, a naphthylethyl group, a naphthylisopropyl group, a pyrrolylmethyl group, a pyrrolylethyl group, an aminobenzyl group, a nitrobenzyl group, a cyanobenzyl group, a 1-hydroxy-2-phenylisopropyl group, a 1-chloro-2-phenylisopropyl group, and the like, but are not limited thereto.

In the present specification, the alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the aryl group may be monocyclic, and the number of carbon atoms thereof is not particularly limited, but is preferably 6 to 60. Specific examples of the aryl group include a monocyclic aromatic group, such as a phenyl group, a biphenyl group, and a terphenyl group, a polycyclic aromatic group, such as a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group, and the like, but are not limited thereto.

In the present specification, the fluorenyl group may be substituted, and adjacent substituents may combine with each other to form a ring.

When the fluorenyl group is substituted, the fluorenyl group may be

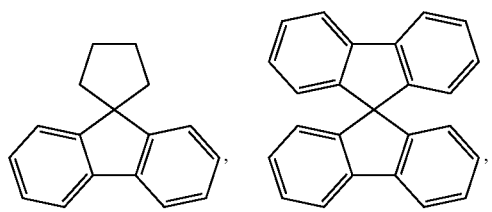

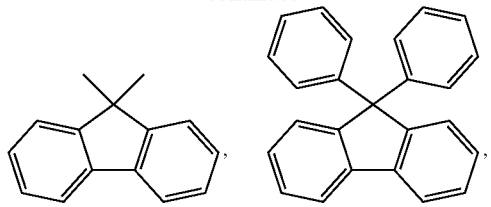

and the like. However, the fluorenyl group is not limited thereto.

In the present specification, a hetero-cyclic group or a heteroaryl group includes one or more of an atom other than carbon, that is, a heteroatom, and specifically, the heteroatom may include one or more atoms selected from the group consisting of O, N, and S, and the like. The number of carbon atoms of the hetero-cyclic group is not particularly limited, but is preferably 2 to 60. Examples of the hetero-cyclic group include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a dibenzofuranyl group, and the like, but are not limited thereto.

In the present specification, the heteroaryl in the heteroaryloxy group may be selected from the above-described examples of the heteroaryl group. In the present specification, the aryl group in the aryloxy group, the arylthioxy group, the arylsulfoxy group, and the aralkylamine group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, the alkyl group in the alkylthioxy group, the alkylsulfoxy group, the alkylamine group, and the aralkylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The two or more arylamine groups which the aryl group includes may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the heteroaryl group in the heteroarylamine group may be selected from the above-described examples of the heterocyclic group.

In the present specification, an alkylene group, an alkenylene group, and an arylene group each mean that there are two bonding positions in an alkyl group, an alkenyl group, and an aryl group, that is, a divalent group. The above-described description on the alkyl group and the aryl group may be applied, except that the alkylene group, the alkenylene group, and the arylene group are a divalent group.

In the present specification, a case where adjacent groups combine with each other to form a hydrocarbon ring or a hetero ring means that adjacent substituents form a bond to form a 5- to 8-membered monocyclic or polycyclic hydrocarbon ring or a 5- to 8-membered monocyclic or polycyclic hetero ring including one or more heteroatoms.

In the present specification, the hydrocarbon ring includes all of a cycloalkyl group; a cycloalkenyl group; an aromatic ring group; or an aliphatic ring group, may be monocyclic or polycyclic, and includes all of the rings fused by combining one or two or more of these groups.

The hetero ring formed in the present specification means those in which at least one carbon atom of the hydrocarbon rings is substituted with a heteroatom, may be an aliphatic ring or an aromatic ring, and may be monocyclic or polycyclic.

In another exemplary embodiment, the organic solar cell has a normal structure in which the first electrode is an anode, and the second electrode is a cathode.

The normal structure may mean that an anode is formed on a substrate. Specifically, according to an exemplary embodiment of the present specification, when the organic solar cell has a normal structure, a first electrode to be formed on a substrate may be an anode.

FIG. 1 illustrates an example of the organic solar cell according to an exemplary embodiment of the present specification. Specifically, FIG. 1 illustrates an organic solar cell having a normal structure. In FIG. 1, ITO is provided as an anode on a substrate, and a PEDOT:PSS layer is formed as a buffer layer on the anode. Further, P3HT:PCBM is used as a photoactive layer, a layer including a fullerene derivative substituted with a crown-type substituent and the photoactive layer are simultaneously formed, and a cathode is formed by using Al. The fullerene derivative substituted with the crown-type substituent is mixed with a photoactive layer material to form a separate layer through the self-phase separation.

However, the organic solar cell according to an exemplary embodiment of the present specification is not limited to the structure and material in FIG. 1, an additional layer may be provided, and each layer may be constituted by using various materials.

In an exemplary embodiment of the present specification, the organic solar cell has an inverted structure in which the first electrode is a cathode, and the second electrode is an anode.

The inverted structure may mean that a cathode is formed on a substrate. Specifically, according to an exemplary embodiment of the present specification, when the organic solar cell has an inverted structure, a first electrode to be formed on a substrate may be a cathode.

FIG. 2 illustrates an example of the organic solar cell according to an exemplary embodiment of the present specification. Specifically, FIG. 2 illustrates an organic solar cell having an inverted structure. In FIG. 2, ITO is provided as a cathode on a substrate, and a buffer layer is formed on the cathode by using ZnO. In addition, P3HT:PCBM is used as a photoactive layer, a layer including a fullerene derivative substituted with a crown-type substituent and the photoactive layer are simultaneously formed, and $MoO_3/Al$ is formed as an anode.

However, the solar cell according to an exemplary embodiment of the present specification is not limited to the structure and material in FIG. 2, an additional layer may be provided, and each layer may be constituted by using various materials.

In an exemplary embodiment of the present specification, the organic solar cell further includes one or two or more organic material layers selected from the group consisting of a hole injection layer, a hole transport layer, a hole blocking layer, a charge generation layer, an electron blocking layer, an electron injection layer, and an electron transport layer.

In an exemplary embodiment of the present specification, the organic solar cell has an inverted structure in which the first electrode is a cathode and the second electrode is an anode, a cathode buffer layer is provided between the first electrode and the photoactive layer, and an anode buffer layer is provided between the second electrode and the photoactive layer.

An exemplary embodiment of the present specification may further include another organic material layer in addition to the anode buffer layer and the cathode buffer layer. Another exemplary embodiment may include only one of the anode buffer layer and the cathode buffer layer, and may not include the buffer layer.

In still another exemplary embodiment, the organic solar cell has a normal structure in which the first electrode is an anode and the second electrode is a cathode, an anode buffer layer is provided between the first electrode and the photoactive layer, and a cathode buffer layer is provided between the second electrode and the photoactive layer.

In an exemplary embodiment of the present specification, the cathode buffer layer may be an electron transport layer.

In an exemplary embodiment of the present specification, the anode buffer layer may be a hole transport layer.

The first electrode of the present specification may be a cathode electrode, and may be a transparent conductive oxide layer or a metal electrode.

When the first electrode is a transparent electrode, the first electrode may be a conductive oxide, such as indium tin oxide (ITO) or indium zinc oxide (IZO). Furthermore, the first electrode may also be a semi-transparent electrode. When the first electrode is a semi-transparent electrode, the first electrode may be prepared by using a semi-transparent metal such as Ag, Au, Mg, Ca, or an alloy thereof. When a semi-transparent metal is used as a first electrode, the organic solar cell may have a micro cavity structure.

When the electrode of the present specification is a transparent conductive oxide layer, as the electrode, it is possible to use an electrode in which a conductive material is doped onto a flexible and transparent material such as plastic including polyethylene terephthalate (PET), polyethylene naphthalate (PEN), polypropylene (PP), polyimide (PI), polycarbornate (PC), polystyrene (PS), polyoxymethylene (POM), an acrylonitrile styrene copolymer (AS resin), an acrylonitrile butadiene styrene copolymer (ABS resin), triacetyl cellulose (TAC), and polyarylate (PAR) in addition to glass and a quartz plate. Specifically, the electrode may be indium tin oxide (ITO), fluorine doped tin oxide (FTO), aluminum doped zinc oxide (AZO), indium zinc oxide (IZO), $ZnO—Ga_2O_3$, $ZnO—Al_2O_3$, antimony tin oxide (ATO), and the like, and more specifically, the electrode may be ITO.

In an exemplary embodiment of the present specification, the second electrode may be an anode, and the second electrode may be a metal electrode. Specifically, the metal electrode may include one or two or more selected from the group consisting of silver (Ag), aluminum (Al), platinum (Pt), tungsten (W), copper (Cu), molybdenum (Mo), gold (Au), nickel (Ni), and palladium (Pd). More specifically, the metal electrode may be silver (Ag).

In an exemplary embodiment of the present specification, in the forming of the first electrode and/or the second electrode, a patterned ITO substrate is sequentially cleaned with a cleaner, acetone, and isopropanol (IPA), and then dried on a hot plate at 100° C. to 250° C. for 1 minute to 30 minutes, specifically at 250° C. for 10 minutes, in order to remove moisture, and when the substrate is completely cleaned, the surface of the substrate may be hydrophilically modified. As a pre-treatment technology for this purpose, it is possible to use a) a surface oxidation method using a parallel flat plate-type discharge, b) a method of oxidizing the surface through ozone produced by using UV rays in a vacuum state, c) an oxidation method using oxygen radicals produced by plasma, and the like. The junction surface potential may be maintained through a surface modification as described above at a level suitable for the surface potential of the hole injection layer, and a polymer thin film is easily formed on an ITO substrate and the quality of the thin film may be improved. Depending on the condition of the substrate, one of the methods is selected, and whatever method is used, a substantial effect of the pre-treatment may be commonly expected only when oxygen is prevented from leaving from the surface of the substrate and moisture and organic materials are maximally inhibited from remaining.

In the Examples of the present specification described below, the method of oxidizing the surface through ozone produced by using UV was used, and after ultrasonic cleaning, the patterned ITO substrate was baked and dried well on a hot plate, introduced into the next chamber, and an UV lamp was actuated to clean the patterned ITO substrate by ozone produced by reacting oxygen gas with UV light. However, the method of modifying the surface of the patterned ITO substrate in the present invention need not be particularly limited, and any method may be used as long as the method is a method of oxidizing a substrate.

In an exemplary embodiment of the present specification, the organic solar cell has an inverted structure. When the organic solar cell according to an exemplary embodiment of the present specification has an inverted structure, the second electrode may be silver (Ag) or $MoO_3/Al$.

The organic solar cell having the inverted structure according to the present specification may mean that an anode and a cathode of an organic solar cell having a general structure are constituted in a reverse direction. An Al layer used in an organic solar cell having a general structure is very vulnerable to an oxidation reaction in the air, has difficulty in being used as an ink, and thus has a limitation in commercialization through a printing process. However, since Ag may be used instead of Al, the organic solar cell having the inverted structure according to the present specification is more stable to the oxidation reaction than an organic solar cell having a general structure and facilitates the preparation of an Ag ink, and accordingly, there is an advantage in that the organic solar cell is advantageous in commercialization through a printing process.

According to an exemplary embodiment of the present specification, the organic solar cell may have a normal structure. When the organic solar cell according to an exemplary embodiment of the present specification has a normal structure, the second electrode may be Al.

In an exemplary embodiment of the present specification, the charge transport layer includes one or two or more selected from the group consisting of conductive oxides, metal carbides, and metals.

In another exemplary embodiment, the charge transport layer includes one or more selected from the group consisting of titanium oxide; zinc oxide; and cesium carbonate.

In the present specification, the charge transport layer means a layer which transports "holes" or "electrons", and may be an electron transport layer or a hole transport layer.

According to an exemplary embodiment of the present specification, a conductive oxide of the electron transport layer may be electron-extracting metal oxides, and specifically, may include one or more selected from the group consisting of titanium oxide ($TiO_x$); zinc oxide (ZnO); and cesium carbonate ($Cs_2CO_3$).

According to an exemplary embodiment of the present specification, the metal may be a core shell material including silver (Ag) nanoparticle, gold (Au) nanoparticle, and a metal oxide such as $Ag—SiO_2$, $Ag—TiO_2$, and $Au—TiO_2$. The core shell material includes a metal as a core, and a metal oxide such as $Ag—SiO_2$, $Ag—TiO_2$, and $Au—TiO_2$ as a shell.

The electron transport layer may be formed by using sputtering, E-Beam, thermal deposition, spin coating, screen printing, inkjet printing, doctor blade, or a gravure printing method to be applied on one surface of a first electrode or to be coated in the form of a film.

In exemplary embodiments of the present specification, the photoactive layer includes an electron donor material and an electron acceptor material as a photoactive material. In the present specification, the photoactive material may mean the electron donor material and the electron acceptor material.

In the photoactive layer, the electron donor material forms an exciton in which an electron and a hole form a pair by photoexcitation, and the exciton is divided into an electron and a hole at the interface of electron donor/electron acceptor. The separated electron and hole move to the electron donor material and the electron acceptor material, respectively, and the electron and hole may be collected in the first electrode and the second electrode to be used in the outside as an electric energy.

Further, in an exemplary embodiment of the present specification, the photoactive layer may have a bulk heterojunction structure or a double layer junction structure. The bulk heterojunction structure may be a bulk heterojunction (BHJ) junction type, and the double layer junction structure may be a bi-layer junction type.

In an exemplary embodiment of the present specification, a mass ratio of the electron donor material and the electron acceptor material may be 1:10 to 10:1. Specifically, the mass ratio of the electron acceptor material and the electron donor material in the present specification may be 1:0.5 to 1:5.

According to an exemplary embodiment of the present specification, the electron donor material may include: at least one electron donor; or a polymer of at least one electron acceptor and at least one electron donor. The electron donor material may include at least one electron donor. In addition, the electron donor material includes a polymer of at least one electron acceptor and at least one electron donor.

Specifically, the electron donor material may be various polymeric materials such as thiophene-based, fluorene-based, and carbazole-based materials, and a single molecular material, starting from poly[2-methoxy-5-(2'-ethyl-hexyloxy)-1,4-phenylene vinylene] (MEH-PPV).

Specifically, the single molecular material may include one or more materials selected from the group consisting of copper (II) phthalocyanine, zinc phthalocyanine, tris[4-(5-dicyanomethylidenemethyl-2-thienyl)phenyl]amine, 2,4-bis [4-(N,N-dibenzylamino)-2,6-dihydroxyphenyl]squaraine, benz[b]anthracene, and pentacene. Specifically, the polymeric material may include one or more materials selected from the group consisting of poly 3-hexyl thiophene (P3HT), poly[N-9'-heptadecanyl-2,7-carbazole-alt-5,5-(4'-7'-di-2-thienyl-2',1',3'-benzothiadiazole)] (PCDTBT), poly [2,6-(4,4-bis-(2,ethylhexyl)-4H-cyclopenta[2,1-b;3,4-b']dithiophene)-alt-4,7-(2,1,3-benxothiadiazole)] (PCPDTBT), poly[2,7-(9,9-dioctyl-fluorene)-alt-5,5-(4,7-di 2-thienyl-2,1, 3-benzothiadiazole)] (PFO-DBT), poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b] thiophenediyl]] (PTB7), and poly[2,7-(9,9-dioctyl-dibenzosilole)-alt-4,7-bis(thiophen-2-yl)benzo-2,1,3-thiadiazole] (PSiF-DBT).

In an exemplary embodiment of the present specification, the electron acceptor material may be a fullerene derivative or a non-fullerene derivative.

In an exemplary embodiment of the present specification, the fullerene derivative is a C60 to C90 fullerene derivative. Specifically, the fullerene derivative may be a C60 fullerene derivative or a C70 fullerene derivative.

According to an exemplary embodiment of the present specification, the C60 fullerene derivative or the C70 fullerene derivative is each independently selected from the group consisting of hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; and a substituted or unsubstituted hetero-cyclic group, or two adjacent substituents may be additionally substituted with a substituent which forms a fused ring.

In an exemplary embodiment of the present specification, the fullerene derivative may be selected from the group consisting of a C76 fullerene derivative, a C78 fullerene derivative, a C84 fullerene derivative, and a C90 fullerene derivative.

In an exemplary embodiment of the present specification, the C76 fullerene derivative, the C78 fullerene derivative, the C84 fullerene derivative, and the C90 fullerene derivative are each independently selected from the group consisting of hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; and a substituted or unsubstituted hetero-cyclic group, or two adjacent substituents may be additionally substituted with a substituent which forms a fused ring.

The fullerene derivative has excellent ability to separate an electron-hole pair (exciton) and excellent charge mobility compared to the non-fullerene derivative, and thus is advantageous in efficiency characteristics.

In the photoactive layer according to an exemplary embodiment of the present specification, an electron donor material and an electron acceptor material may form a bulk heterojunction (BHJ). The photoactive layer of the present specification may be annealed at 30° C. to 300° C. for 1 second to 24 hours in order to maximize the characteristics after the electron donor material and the electron acceptor material are mixed with each other.

In an exemplary embodiment of the present specification, the photoactive layer may include poly 3-hexyl thiophene (P3HT) as an electron donor material and [6,6]-phenyl-$C_{61}$-butyric acid methyl ester ($PC_{61}BM$) and/or [6,6]-phenyl-$C_{71}$-butyric acid methyl ester ($PC_{71}BM$) as an electron acceptor material.

In an exemplary embodiment of the present specification, a mass ratio of the electron donor material and the electron acceptor material may be 1:0.4 to 1:2, and specifically 1:0.7. However, the photoactive layer is not limited to only the materials.

The photoactive materials as described above are dissolved in an organic solvent, and then the solution is applied to have a thickness in a range of 50 nm to 280 nm by a method such as spin coating to introduce a photoactive layer. In this case, it is possible to apply a method, such as dip coating, screen printing, spray coating, doctor blade, and brush painting, to the photoactive layer.

In addition, in the electron acceptor, other fullerene derivatives including $PC_{61}BM$, such as C70, C76, C78, C80, C82, and C84 may also be used, and the crystallinity of the conductive polymer may be enhanced by subjecting the coated thin film to a heat treatment at 80° C. to 160° C. Specifically, the organic solar cell of the present specification has an inverted structure, and in this case, a pre-annealing may be carried out at 120° C.

The hole transport layer and/or electron transport layer material(s) of the present specification may be a material which enhances the probability that the produced charges are transported to electrodes by efficiently transferring electrons and holes to a photoactive layer, but are/is not particularly limited.

According to an exemplary embodiment of the present specification, the hole transport layer may be an anode buffer layer.

The hole transport layer may be introduced into the upper portion of the pre-treated photoactive layer by a method such as spin coating, dip coating, inkjet printing, gravure printing, spray coating, doctor blade, bar coating, gravure coating, brush painting, and thermal deposition. In this case, poly(3,5-ethylenedioxythiophene):poly(4-styrenesulfonate) [PEDOT:PSS] is usually used as the conductive polymer solution, and it is possible to use molybdenum oxide ($MoO_x$), vanadium oxide ($V_2O_5$), nickel oxide (NiO), tungsten oxide (WO), and the like as the hole-extracting metal oxide material. According to an exemplary embodiment of the present specification, the hole transport layer may be formed by depositing $MoO_3$ to have a thickness of 5 nm to 10 nm through a thermal deposition system.

According to an exemplary embodiment of the present specification, the organic solar cell may further include a substrate. Specifically, the substrate may be provided at the lower portion of the first electrode.

According to an exemplary embodiment of the present specification, as the substrate, it is possible to use a substrate having excellent transparency, surface smoothness, ease of handling, and water-proof property. Specifically, a glass substrate, a thin film glass substrate, or a transparent plastic substrate may be used. The plastic substrate may include a film such as polyethylene terephthalate (PET), polyethylene naphthalate (PEN), polyether ether ketone (PEEK), and polyimide (PI) in the form of a single layer or multi-layers. However, the substrate is not limited thereto, and a substrate typically used for an organic solar cell may be used.

According to an exemplary embodiment of the present specification, the organic solar cell may have a wound structure. Specifically, the organic solar cell may be manufactured in the form of a flexible film, and may be made as a solar cell having a hollow wound structure in which the film is wound in a cylindrical form. When the organic solar cell has a wound structure, the organic solar cell may be installed in a manner in which the organic solar cell is stood up on the ground. In this case, at the position in which the organic solar cell is installed, it is possible to secure a portion in which the incident angle of light becomes a maximum while the sun moves from the east to the west. Accordingly, there is an advantage in that light may be absorbed as much as possible and the efficiency may be enhanced while the sun is rising.

The present specification provides a method for manufacturing the above-described organic solar cell, the method including: preparing a substrate; forming a first electrode on the substrate; forming an organic material layer having two or more layers including a photoactive layer and a layer including a fullerene derivative having a crown-type substituent, on the first electrode; and forming a second electrode on the organic material layer.

In an exemplary embodiment of the present specification, the forming of the organic material layer includes coating a composition including a photoactive layer material and a material for a layer including a fullerene derivative, and the photoactive layer and the fullerene layer are simultaneously formed by the phase separation of the photoactive layer material and the material for the layer including the fullerene derivative.

In the process of the organic solar cell, when a buffer layer provided between the photoactive layer and the first electrode or the second electrode is manufactured, the buffer layer has a thin thickness, so that it is not easy to adjust the thickness of the buffer layer or uniformly manufacture the buffer layer during the process.

In an exemplary embodiment of the present specification, the material for the layer including a fullerene derivative having a crown-type substituent may be mixed with a photoactive layer material to be together coated when the photoactive layer is manufactured.

In this case, the material for the layer including the fullerene derivative includes a self-phase separation unit, that is, a crown-type substituent, and thus, the material for the layer may form a double layer of a photoactive layer and a layer including a fullerene derivative. The layer including the fullerene derivative acts as a buffer layer in the organic solar cell, and thus may form a double layer of a photoactive layer and a layer including a fullerene derivative by a single process without a separate process of manufacturing the buffer layer.

In this case, in a mixed solution of a photoactive layer material and a material for a layer including a fullerene derivative, an amount of material for a layer including a fullerene derivative may be adjusted to adjust the thickness of the layer including the fullerene derivative and form a uniform layer.

Further, the concentration of the layer including a fullerene derivative and/or a substituent to be substituted into the fullerene derivative may be adjusted such that the layer is provided on one surface of the photoactive layer, which is close to the first electrode, or one surface of the photoactive layer, which is close to the second electrode, and accordingly, it is possible to adjust the position of the layer including a fullerene derivative, which serves as a buffer layer.

In an exemplary embodiment of the present specification, the ratio of the electron donor material of the photoactive layer material and the material for the layer including the fullerene derivative is 0.01 wt % to 0.2 wt %. In an exemplary embodiment of the present specification, the ratio of the electron donor material of the photoactive layer material and the material for the layer including the fullerene derivative is 0.05 wt % to 0.1 wt %.

In the organic solar cell according to an exemplary embodiment of the present specification, the layer including the fullerene derivative, the first electrode, the second electrode, the photoactive layer, the layer including the fullerene derivative, the fullerene derivative, and the crown-type substituent are the same as those described above.

In the present specification, a generally used method may be used, except for the forming of the organic material layer having two or more layers, which includes the photoactive layer and the layer including the fullerene derivative.

MODE FOR INVENTION

Hereinafter, the present specification will be described in detail with reference to the Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

Preparation Example 1. Preparation of Chemical Formula 2-2-1

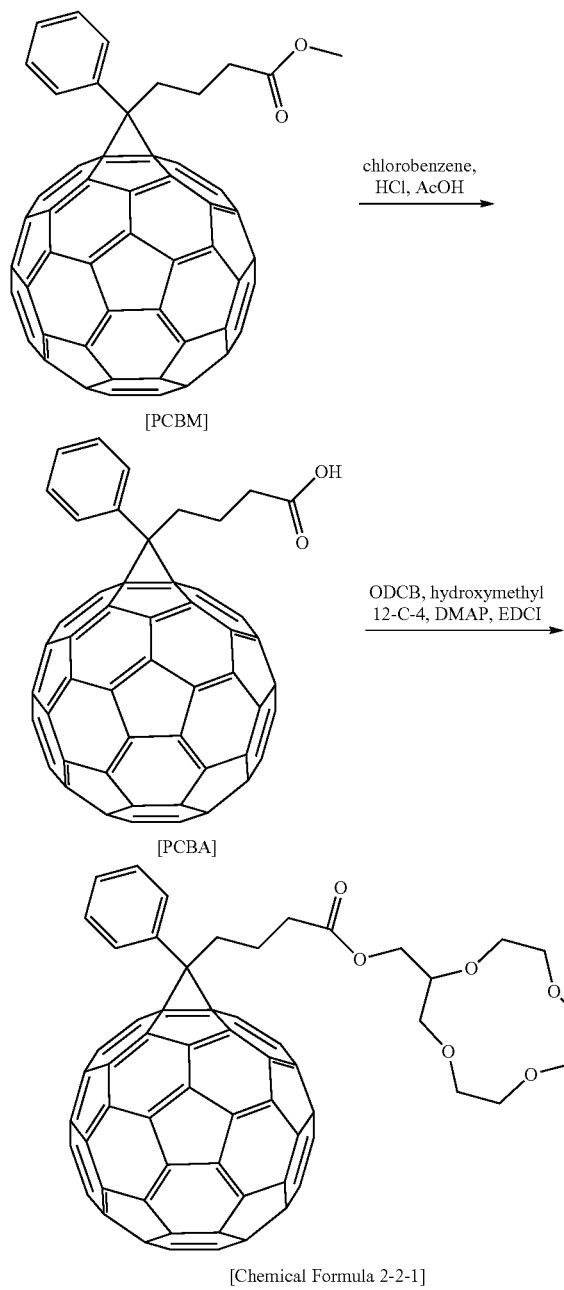

[Chemical Formula 2-2-1]

1 g of PCBM was put into 80 ml of chlorobenzene, and the resulting mixture was subjected to reflux reaction at 180° C. for approximately 1 hour. 8 ml of hydrochloric acid and 20 ml of acetic acid were added thereto, and then the resulting mixture was subjected to reflux reaction at 180° C. for 16 hours. Whether PCBM disappeared was confirmed by TLC, and then the solution was concentrated until the amount of solvent became approximately 30 ml. PCBA, which is a sold sample obtained by precipitation with methanol, was filtered and dried. (yield=89%)

120 mg of the dried PCBA was put into approximately 5 ml of o-dichlorobenzene, and 0.067 ml of hydroxymethyl 12-C-4, 33 mg of 4-dimethylaminopyridine, and 51.4 mg of 1-ethyl-3-(3-dimethylaminopropyl)carbodiimide (EDCI) were added thereto at 0° C. The mixture was stirred for 12 hours while gradually increasing the temperature from 0° C. to room temperature. When the reaction was terminated, column purification was carried out to obtain a desired compound. (yield=10%)

FIG. 3 is a view illustrating the MS graph of a fullerene derivative of Chemical Formula 2-2-1 prepared above.

Preparation Example of Organic Solar Cell

An ITO glass was subjected to ultrasonication in each of acetone and ethanol for 30 minutes and washed. After the washing, the surface was treated for 15 minutes by using UVO, and PEDOT:PSS was coated on the surface-treated ITO glass, and then a heat treatment was carried out at 200° C. for 5 minutes. After the heat treatment, a P3HT:PCBM solution mixed at a ratio of 1:0.7 was coated to form a thin film having a thickness of approximately 220 nm, and then a heat treatment was carried out at 110° C. for 10 minutes. An Al electrode was deposited to have a thickness of 100 nm at $1\times10^{-7}$ torr.

Example 1

An organic solar cell was manufactured in the same manner as in the Preparation Example of the organic solar cell, except that a $Li^+$ ion composite of the fullerene derivative of Chemical Formula 2-2-1 prepared through the Preparation Example was added in an amount of 1% based on the total weight of the photoactive layer to the P3HT:PCBM solution in the Preparation Example.

Example 2

An organic solar cell was manufactured in the same manner as in the Preparation Example of the organic solar cell, except that a $Li^+$ ion composite of the fullerene derivative of Chemical Formula 2-2-1 prepared through the Preparation Example was added in an amount of 3% based on the total mass of the photoactive layer to the P3HT:PCBM solution in the Preparation Example.

Example 3

An organic solar cell was manufactured in the same manner as in the Preparation Example of the organic solar cell, except that a $Li^+$ ion composite of the fullerene derivative of Chemical Formula 2-2-1 prepared through the Preparation Example was added in an amount of 5% based on the total mass of the photoactive layer to the P3HT:PCBM solution in the Preparation Example.

Example 4

An organic solar cell was manufactured in the same manner as in the Preparation Example of the organic solar cell, except that the fullerene derivative of Chemical Formula 2-2-1 prepared through the Preparation Example was added in an amount of 1% based on the total mass of the photoactive layer to the P3HT:PCBM solution in the Preparation Example.

Comparative Example 1

An organic solar cell was manufactured in the same manner as in the Preparation Example of the organic solar cell, except that LiF was vacuum-deposited to have a thickness of 0.7 nm at a degree of vacuum of 1×10$^{-7}$ torr, and after the vacuum deposition, an Al electrode was deposited to have a thickness of 100 nm at 1×10$^{-7}$ torr.

The photoelectric conversion characteristics of the organic solar cells manufactured according to the Experimental Examples and the Comparative Example are shown in the following Table 1.

TABLE 1

|  | $V_{oc}$ (V) | $J_{sc}$ (mA/cm$^2$) | FF | PCE (%) |
| --- | --- | --- | --- | --- |
| Comparative Example 1 | 0.608 | 9.48 | 0.575 | 3.31 |
| Example 1 | 0.610 | 9.60 | 0.578 | 3.38 |
| Example 2 | 0.618 | 10.10 | 0.591 | 3.69 |
| Example 3 | 0.626 | 10.55 | 0.608 | 4.02 |
| Example 4 | 0.615 | 9.98 | 0.589 | 3.62 |

In the present specification, $V_{oc}$, $J_{sc}$, FF, and PCE mean an open-circuit voltage, a current density or a short-circuit current, a fill factor, and energy conversion efficiency, respectively. The open-circuit voltage and the short-circuit current are an X axis intercept and an Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open circuit voltage. The energy conversion efficiency may be obtained when these three values are divided by the intensity of the irradiated light, and the higher value is preferred.

When the physical properties of the organic solar cells according to the Comparative Example and the Examples in Table 1 are compared with each other, it can be seen that the organic solar cells of Examples 1 to 4 exhibited higher fill factors and/or higher efficiencies than those of Comparative Examples 1 and 2.

The invention claimed is:

1. An organic solar cell comprising:
a first electrode;
a second electrode facing the first electrode;
a photoactive layer between the first electrode and the second electrode; and
a layer comprising a fullerene derivative, wherein the layer is in contact with the photoactive layer,
wherein the fullerene derivative comprises a crown-type substituent, and
wherein the layer comprising the fullerene derivative comprises a fullerene derivative of Chemical Formula 1:

[Chemical Formula 1]

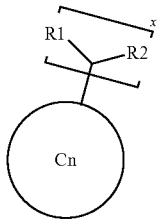

wherein:
Cn is a $C_{60}$ to $C_{120}$ fullerene;
x is an integer of 1 to 10;
at least one of R1 and R2 is -(L)a-(Y),
a is an integer of 0 to 4,
when a is 2 or more, two or more L are the same as or different from each other,
L is a substituted or unsubstituted divalent ester group, a substituted or unsubstituted divalent thioester group, a substituted or unsubstituted divalent thionoester group, a divalent ketone group, a divalent thione group, a divalent carbonyl group, a substituted or unsubstituted alkylene group, a substituted or unsubstituted alkenylene group, a substituted or unsubstituted arylene group, or a substituted or unsubstituted divalent heterocyclic group;
Y is a crown-type substituent;
when R1 or R2 is not -(L)a-(Y), R1 or R2 is hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted hetero-cyclic group; and
Chemical Formula 1 is optionally additionally substituted with a substituent selected from the group consisting of hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, and a substituted or unsubstituted hetero-cyclic group.

2. The organic solar cell of claim 1, wherein the photoactive layer comprises a photoactive layer material comprising one or two or more materials selected from the group consisting of an electron acceptor material and an electron donor material, and
the layer comprising the fullerene derivative is formed by a phase separation of the photoactive layer material and a material for the layer comprising the fullerene derivative.

3. The organic solar cell of claim 1, wherein Y is represented by the following structure:

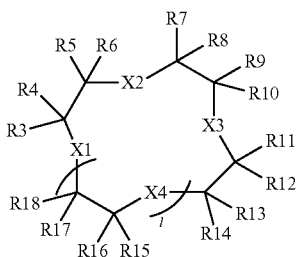

wherein:
l is a repeating number of a structure in the parenthesis and is an integer of 1 to 3, and
when l is 2 or more, two or more structures in the parenthesis are the same as or different from each other;
X1 to X4 are the same as or different from each other, and each is independently O, S, or NR; and
R and R3 to R18 are the same as or different from each other, and each is independently hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted hetero-cyclic group, or adjacent substituents combine with each other to form a substituted or unsubstituted hydrocarbon ring, or a substituted or unsubstituted hetero ring, and any one of R3 to R18 is linked to -(L)a-.

4. The organic solar cell of claim 1, wherein L is a substituted or unsubstituted divalent ester group, a substituted or unsubstituted alkylene group, or a substituted or unsubstituted arylene group.

5. The organic solar cell of claim 1, further comprising an ionic group provided at a center of the crown-type substituent.

6. The organic solar cell of claim 1, wherein a content of the fullerene derivative comprising the crown-type substituent is 1 wt % to 15 wt % at an interface of the photoactive layer and the layer comprising the fullerene derivative.

7. The organic solar cell of claim 1, wherein the organic solar cell has an inverted structure in which the first electrode is a cathode and the second electrode is an anode.

8. The organic solar cell of claim 1, wherein the organic solar cell has a normal structure in which the first electrode is an anode and the second electrode is a cathode.

9. The organic solar cell of claim 1, wherein the organic solar cell further comprises an organic material comprising one or two or more layers selected from the group consisting of a hole injection layer, a hole transport layer, a hole blocking layer, a charge generation layer, an electron blocking layer, an electron injection layer, and an electron transport layer.

10. A method for manufacturing the organic solar cell of claim 1, the method comprising:
preparing a substrate;
forming the first electrode on the substrate;
forming an organic material layer comprising two or more layers, wherein the organic material layer comprises the photoactive layer and the layer comprising the fullerene derivative that comprises the crown-type substituent, on the first electrode; and
forming the second electrode on the organic material layer.

11. The method of claim 10, wherein the forming of the organic material layer comprises coating a composition comprising a material for the photoactive layer and a material for the layer comprising the fullerene derivative, and
the photoactive layer and the layer comprising the fullerene derivative are simultaneously formed by a phase separation of the material for the photoactive layer and the material for the layer comprising the fullerene derivative.

12. The organic solar cell of claim 1, wherein Chemical Formula 1 is Chemical Formula 1-1:

[Chemical Formula 1-1]

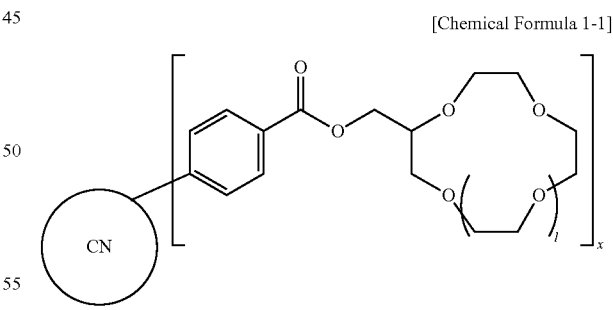

wherein:
CN is a $C_{60}$ to $C_{120}$ fullerene;
x is an integer of 1 to 10; and
l is an integer of 1 to 3.

13. The organic solar cell of claim 1, wherein the layer comprising the fullerene derivative has a thickness of 1 nm to 30 nm.

14. An organic solar cell comprising:
a first electrode;
a second electrode facing the first electrode;

a photoactive layer between the first electrode and the second electrode; and a layer comprising a fullerene derivative, wherein the layer is in contact with the photoactive layer, wherein the fullerene derivative comprises a crown-type substituent, and wherein is the layer comprising the fullerene derivative comprises a fullerene derivative of Chemical Formula 2-1:

[Chemical Formula 2-1]

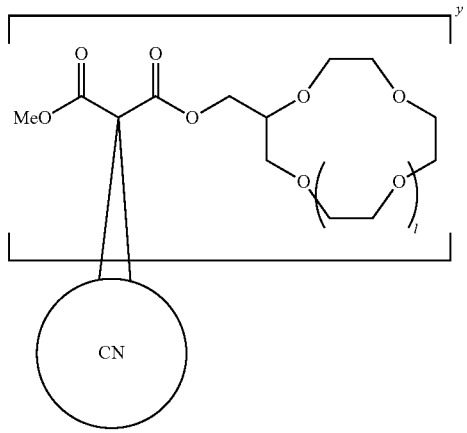

wherein:
CN is a $C_{60}$ to $C_{120}$ fullerene;
y is an integer of 1 to 10; and
l is an integer of 1 to 3.

15. An organic solar cell comprising:
a first electrode;
a second electrode facing the first electrode;
a photoactive layer between the first electrode and the second electrode; and
a layer comprising a fullerene derivative, wherein the layer is in contact with the photoactive layer,
wherein the fullerene derivative comprises a crown-type substituent, and
wherein the layer comprising the fullerene derivative comprises a fullerene derivative of Chemical Formula 3:

[Chemical Formula 3]

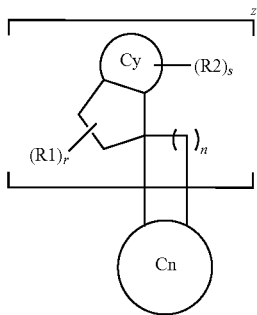

wherein:
Cn is a $C_{60}$ to $C_{120}$ fullerene;
n is an integer of 0 to 3;
z is an integer of 1 to 10;

at least one of R1 and R2 is -(L)a-(Y),
a is an integer of 0 to 4,
when a is 2 or more, two or more L are the same as or different from each other,
L is a substituted or unsubstituted divalent ester group, a substituted or unsubstituted divalent thioester group, a substituted or unsubstituted divalent thionoester group, a divalent ketone group, a divalent thione group, a divalent carbonyl group, a substituted or unsubstituted alkylene group, a substituted or unsubstituted alkenylene group, a substituted or unsubstituted arylene group, or a substituted or unsubstituted divalent heterocyclic group;
Y is a crown-type substituent;
Cy is a substituted or unsubstituted monocyclic or polycyclic aromatic hydrocarbon ring, or a substituted or unsubstituted monocyclic or polycyclic hetero ring groups,
when R1 or R2 is not -(L)a-(Y), R1 or R2 is hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted hetero-cyclic group, and R1 and R2 optionally combine with each other to form a monocyclic or polycyclic ring;
r is an integer of 0 to 2;
s is an integer of 0 to 30, and
when r and s are each 2 or more, the structures in the parenthesis are the same as or different from each other; and
Chemical Formula 3 is optionally additionally substituted with a substituent selected from the group consisting of hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, and a substituted or unsubstituted hetero-cyclic group.

16. The organic solar cell of claim 15, wherein Y is represented by the following structure:

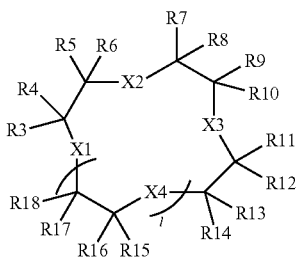

wherein:
l is a repeating number of a structure in the parenthesis and is an integer of 1 to 3, and
when l is 2 or more, two or more structures in the parenthesis are the same as or different from each other;
X1 to X4 are the same as or different from each other, and each is independently O, S, or NR; and
R and R3 to R18 are the same as or different from each other, and each is independently hydrogen, a halogen group, a carboxylic acid group, a nitro group, a nitrile group, an imide group, an amide group, an imine group, thioimide, an anhydride group, a hydroxy group, a substituted or unsubstituted ester group, a substituted or unsubstituted thioester group, a substituted or unsubstituted thionoester group, a substituted or unsubstituted carbonyl group, a substituted or unsubstituted thione group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted hetero-cyclic group, or adjacent substituents combine with each other to form a substituted or unsubstituted hydrocarbon ring, or a substituted or unsubstituted hetero ring, and any one of R3 to R18 is linked to -(L)a-.

17. The organic solar cell of claim 15, wherein L is a substituted or unsubstituted divalent ester group, a substituted or unsubstituted alkylene group, or a substituted or unsubstituted arylene group.

18. The organic solar cell of claim 15, wherein Chemical Formula 3 is Chemical Formula 3-1:

[Chemical Formula 3-1]

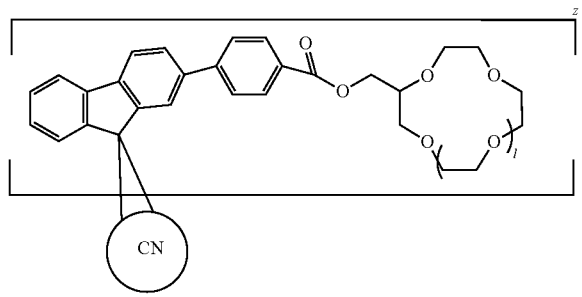

wherein:
CN is a $C_{60}$ to $C_{120}$ fullerene;
z is an integer of 1 to 10; and
l is an integer of 1 to 3.

* * * * *

UNITED STATES PATENT AND TRADEMARK OFFICE
CERTIFICATE OF CORRECTION

PATENT NO.         : 10,439,142 B2
APPLICATION NO.    : 15/303712
DATED              : October 8, 2019
INVENTOR(S)        : Lee et al.

Page 1 of 1

It is certified that error appears in the above-identified patent and that said Letters Patent is hereby corrected as shown below:

In the Claims

Column 33, Line 7, Claim 14:
Please correct "wherein is the layer" to read -- wherein the layer --

Column 35, Line 31, Claim 16:
Please correct "0, S, or NR;" to read -- O, S, or NR; --

Signed and Sealed this
Seventh Day of January, 2020

Andrei Iancu
*Director of the United States Patent and Trademark Office*